United States Patent [19]
Pierce

[11] Patent Number: 5,158,762
[45] Date of Patent: Oct. 27, 1992

[54] WATER-BASED HAIR SPRAY COMPOSITIONS CONTAINING MULTIPLE POLYMERS

[75] Inventor: Deborah R. Pierce, Walnut, Calif.

[73] Assignee: ISP Investments Inc., Wilmington, Del.

[21] Appl. No.: 848,473

[22] Filed: Mar. 9, 1992

[51] Int. Cl.$^5$ .............................................. A61K 7/08
[52] U.S. Cl. ...................................... 424/47; 424/70; 424/71; 424/401; 424/78.03
[58] Field of Search .............................. 424/71, 47, 70

[56] References Cited

U.S. PATENT DOCUMENTS

| | | | |
|---|---|---|---|
| 3,937,802 | 2/1976 | Fujimoto et al. | 424/47 |
| 4,223,009 | 9/1980 | Chakrabarti | 424/47 |
| 4,946,932 | 8/1990 | Jenkins | 528/272 |
| 4,961,921 | 10/1990 | Chuang et al. | 424/47 |
| 5,068,099 | 11/1991 | Sramek | 424/47 |

OTHER PUBLICATIONS

Chemical Formulary, p. 227, vol. XXVII, '89.

Primary Examiner—Thurman K. Page
Assistant Examiner—Neil S. Levy
Attorney, Agent, or Firm—Walter Katz; Marilyn J. Maue; Joshua J. Ward

[57] ABSTRACT

A water-based hair spray composition is provided herein which is capable of delivering a fine finishing mist to provide a stiff resin film having excellent hair holding power, with superior shine, and feel, and within a relatively low drying time, approaching that of alcohol-based systems. The composition of the invention attains its unique attributes by including a predetermined blend of at least two hair spray resins, one being a water soluble resin, and the other resin being a water dispersible polyester or polyesteramide.

14 Claims, No Drawings

WATER-BASED HAIR SPRAY COMPOSITIONS CONTAINING MULTIPLE POLYMERS

BACKGROUND OF THE INVENTION

1. Field of the Invention

This invention relates to hair spray resin compositions, and more particularly, to water-based compositions which contain a multiple polymer system.

2. Description of the Prior Art

Present hair spray compositions, both pump spray and aerosol spray formulations, are described in detail in U.S. Pat. Nos. 3,145,147; 4,223,009; and 4,521,402. These compositions generally perform effectively in providing most of the properties considered desirable for hair preparation, including fine spray patterns, prolonged curl retention under humid conditions, good holding power, ease of removability, and resistance to build-up. However, these and other pump formulations available in the art contain a considerable amount of alcohol which is a volatile organic compound (VOC). Aerosol hair spray formulations also require hydrocarbons or other propellants which add to the VOC content of the composition. Recent state legislation, moreover, has required that hair spray compositions have a lower VOC level than is presently found in commercial hairspray compositions. More particularly, it is now necessary that such compositions contain VOC materials at a weight level of no more than 80% of the composition.

Accordingly, it is an object of the present invention to provide new water-based hair spray compositions which meet VOC standards while retaining the effective properties of presently available compositions for hair preparation and treatment.

Another object of the invention is to provide water-based hair spray compositions capable of providing a fine finishing mist at a high resin solids level and which is substantially moisture resistant, which also forms a stiff resin film on the hair of the user, and provides a good hold and curl retention, with superior shine, and feel, and low drying times, which approach the properties of alcohol-based systems.

These and other objects and features of the invention will be made apparent from the following more particular description thereof.

SUMMARY OF THE INVENTION

A water-based hair spray composition is provided herein which is capable of delivering a fine finishing mist at a high resin solids level. The composition provides a stiff resin film having excellent hair holding power, with superior shine, and feel, and low drying times, which properties approach those of alcohol-based systems. The composition of the invention attains its unique attributes by including a predetermined blend of at least two hair spray polymers, one being a water soluble polymer, and the other being a water dispersible polyester or polyesteramide.

DETAILED DESCRIPTION OF THE INVENTION

The composition of the invention comprises
(a) one or more water soluble polymers and
(b) a water dispersible polyester or polyesteramide derived from:
 (1) at least one dicarboxylic acid or ester,
 (2) at least one diol, and
 (3) a difunctional monomer containing an $SO_3M$ group attached to an aromatic nucleus, wherein M is hydrogen, or metal ion or ammonium ion or the cationic radical of an organic amine;

polyesteramide improves the set time (tac-free time) and shine of the water soluble polymers thereby expanding the use of commercially available water soluble polymers into an aqueous-based hair spray composition which has a drying character, time and feel which approaches to an alcohol-based system.

Polymer blends particularly useful herein for incorporation into the hair grooming composition comprise:
(a) about 99 to about 1 wt. % of a water soluble polymer, and
(b) about 1 to about 99 wt. % of a water-dispersible sulfonate group-containing polyester or polyesteramide.

A method for using these hair grooming compositions comprises:
(i) contacting the following:
 A. one or more water soluble polymers, and
 B. a water-dispersible sulfonate group-containing polyester or polyesteramide,
 C. water, and, optionally,
 D. a neutralizing agent to obtain 65 to 100% neutralization based on the acid monomer in the water soluble polymer, including metal hydroxides and aliphatic, cyclic, or aromatic amines;
(ii) applying the composition to hair, and evaporating the solvent, thereby holding the hair in place.

The final hair grooming composition preferably comprises:
(I) about 2 to about 28 weight % of a polymer blend comprising:
 (a) about 99 to about 1 weight % of a water soluble polymer, and
 (b) about 1 to about 99 weight % of a water-dispersible sulfonate group-containing polyester or polyesteramide,
(II) about 98 to about 40 weight % of water,
(III) 0 to about 30 weight % of an alcohol, and
(IV) 0 to about 5 weight % of a neutralizing base sufficient to neutralize the acid groups of the polymer blend.

Water-dispersible polyesters and polyesteramides useful herein are described in detail in U.S. Pat. Nos. 3,734,874; 3,546,008; 4,335,220; and 3,779,993; and are available from Eastman Chemicals as Polymers AQ 38 and 55.

Preferably, the polyester or polyesteramide has an inherent viscosity of from about 0.28 to about 0.38, an acid moiety of from about 75 to about 84 mole % isophthalic acid and conversely from about 25 to about 16 mole % 5-sodiosulfoisophthalic acid, and a glycol moiety of from abut 45 to about 60 mole % diethylene glycol and conversely from about 55 to about 40 mole % 1,4-cyclohexanedimethanol or ethylene glycol or mixtures thereof.

Most preferably, the polyester or polyesteramide comprises an acid moiety comprising from about 80 to about 83 mole % isophthalic acid and conversely from about 20 to about 17 mole % 5-sodiosulfoisophthalic acid, and said glycol moiety comprises from about 52 to about 56 mole % diethylene glycol and conversely from about 48 to about 44 mole % 1,4-cyclohexanedimethanol.

The water soluble polymers useful herein are preferably prepared from monomers of one or more of the following structures:

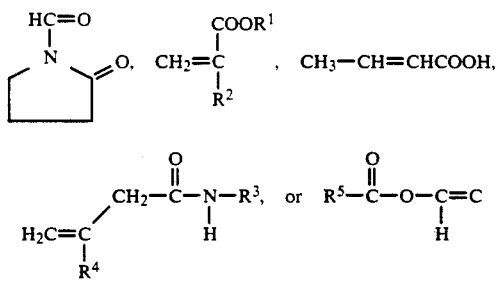

wherein
R¹ is a $C_1$-$C_5$ aliphatic group, preferably a $C_1$-$C_3$ alkyl group, or is of the structure

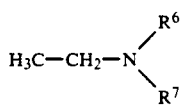

wherein R⁶ and R⁷ are, independently, a $C_1$-$C_5$ alkyl group,
R² is a $C_1$-$C_{10}$ aliphatic group, preferably a $C_1$-$C_3$ alkyl group,
R³ is a $C_1$-$C_{16}$ aliphatic group, preferably a $C_8$ alkyl group,
R⁴ is H or a $C_1$-$C_8$ aliphatic group, preferably H or a $C_8$ group,
R⁵ is a $C_1$-$C_{10}$ aliphatic group, preferably a $C_9$ alkyl group.

Accordingly, suitable water soluble polymers include polyvinyl pyrrolidone (PVP), polyvinyl caprolactam (PVC), polyvinyl acetate (VA), polyacrylates and methacrylates, and copolymers and terpolymers of such monomers, such as VP/VA, VA/crotonic acid/vinyl neodecanoate, VA/crotonic acid, or octylacrylamide/acrylates/butyl aminoethyl methacrylate, VA, mono-n-butyl maleate and isobornyl acrylate; and VP/VC/dimethylaminoethyl methacrylate.

1. Gaffix®VC-713 (GAF Chemicals Corporation) which is a terpolymer derived from the polymerization of vinyl caprolactam, vinylpyrrolidone and an ammonium derivative monomer having from 6-12 carbon atoms selected from the group consisting of dialkyl dialkenyl ammonium halide and a dialkylamino alkyl acrylate or methacrylate (see U.S. Pat. No. 4,521,404). The commercial product is available as a ethanolic solution having a 37% solids level.

2. Gantrez®SP-215 (GAF Chemicals Corporation) is the ethyl half-ester of a linear copolymer of methyl vinyl ether and maleic anhydride.

3. Gantrez®ES-225 (GAF Chemicals Corporation) is the ethyl half-ester of a linear copolymer of methyl vinyl ether and maleic anhydride having a molecular weight of 978,000.

4. Gantrez®ES-425 (GAF Chemicals Corporation) is the butyl half-ester of a linear copolymer of methyl vinyl ether and maleic anhydride having a molecular weight of 1,000,000.

5. Resin 1212 (GAF Chemicals Corporation) is a terpolymer derived from the polymerization of vinyl acetate, mono-n-butyl maleate and isobornyl acrylate (see U.S. Pat. No. 4,689,373), having a molecular weight of about 250,000.

In a preferred embodiment, the polymer blend is prepared as follows: the sulfonate group-containing polymer is prepared, generally by melt polymerization, and an aqueous dispersion containing from about 10% to 30% total solids is prepared from the polyester or polyesteramide directly. Then the water soluble polymer or polymers are added to the aqueous dispersion of the polyester or polyesteramide to produce an aqueous dispersion. The aqueous dispersion so produced can be prepared with a total solids content of from about 1 to about 30. Preferably, the pH is, or is adjusted to be, within the range of about 4-8 in order to minimize hydrolysis of the polyester.

A preferred polymer blend system comprises:
(a) water soluble polymer; GAFFIX®VC-713 (ISP) having the formula:

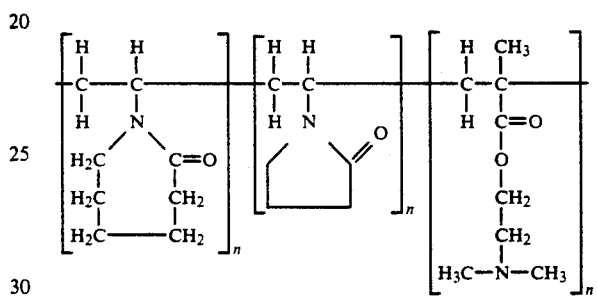

(b) water dispersible polymer Eastman AQ Polymer having the formula:

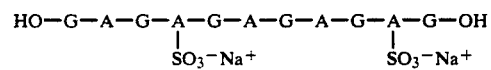

A = An aromatic dicarboxylic acid moiety
B = An aliphatic or cycloaliphatic glycol residue, and
—OH = hydroxy end groups A typical formulation of the composition of the invention is as follows:

| INGREDIENT | EXAMPLE AMOUNT (% BY WT) | SUPPLIER |
|---|---|---|
| Purified Water | 93.06 | |
| Gaffix ® VC-713 (37% in ethanol) | 1.00 | ISP |
| Polymer AQ 55D | 5.00 | Eastman Kodak |
| PVP/VA W 735 | | ISP |
| Crovol A-70 | 0.10 | Croda |
| Panthenol | 0.10 | Tri-K |
| Suttocide A | 0.60 | Sutton |
| Surfadone ® LP-300 | 0.07 | ISP |
| Fragrance | 0.07 | |
| Citric Acid | QS | |
| | 100.00 | |

The above formulation was a one-phase system. Upon testing as a pump hair spray, it was observed that the spray patterns developed were fine, broad and dry, with a soft hold, and excellent shine, and low drying times; the properties were comparable to those of commercial alcohol-based systems.

While the invention has been described with particular reference to certain embodiments thereof, it will be understood that changes and modifications may be made which are within the skill of the art. Accordingly, it is intended to be bound only by the following claims, in which:

What is claimed is:

1. A water-based hair spray composition comprising:
   (a) a water soluble polymer, which is prepared from monomers having one or more of the following structures:

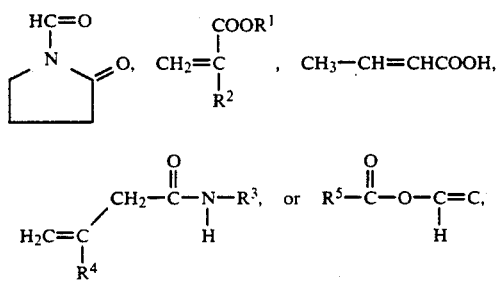

wherein
   $R^1$ is a $C_1$-$C_5$ aliphatic group, preferably a $C_1$-$C_3$ alkyl group, or is of the structure

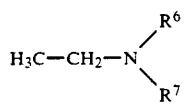

wherein $R^6$ and $R^7$ are, independently, a $C_1$-$C_5$ alkyl group,
   $R^2$ is a $C_1$-$C_{10}$ aliphatic group, preferably a $C_1$-$C_3$ alkyl group,
   $R^3$ is a $C_1$-$C_{16}$ aliphatic group, preferably a $C_8$ alkyl group,
   $R^4$ is H or a $C_1$-$C_8$ aliphatic group, preferably H or a $C_8$ group, and
   $R^5$ is a $C_1$-$C_8$ aliphatic group, preferably $C_9$ alkyl group
   (b) a water dispersible polyester or polyesteramide derived from:
      (1) at least one dicarboxylic acid or ester,
      (2) at least one diol, and
      (3) a difunctional monomer containing an $SO_3M$ group attached to an aromatic nucleus, wherein M is hydrogen, or metal ion or ammonium ion or the cationic radical or an organic amine; and
   (c) water.

2. A water-based hair spray composition according to claim 2 wherein said water soluble polymers include one or more of polyvinyl pyrrolidone (PVP), polyvinyl caprolactam (PVC), polyvinyl acetate (VA), polyacrylates and methacrylates, and copolymers and terpolymers of such monomers, such as VP/VA, VA/crotonic acid/vinyl neodecanoate, VA/crotonic acid, or octylacrylamide/acrylates/butyl aminoethyl methacrylate, VA, mono-n-butyl maleate and isobornyl acrylate.

3. A water-based hair spray composition according to claim 2 in which said water soluble polymer is a terpolymer derived from the polymerization of vinyl caprolactam, vinylpyrrolidone and an ammonium derivative monomer having from 6-12 carbon atoms selected from the group consisting of dialkyl dialkenyl ammonium halide and a dialkylamino alkyl acrylate or methacrylate.

4. A water-based hair spray composition according to claim 2 which is the ethyl or butyl half-ester of a linear copolymer of methyl vinyl ether and maleic anhydride.

5. A water-based hair spray composition according to claim 2 which is a terpolymer derived from the polymerization of vinyl acetate, mono-n-butyl maleate and isobornyl acrylate.

6. A water-based hair spray composition according to claim 1 wherein the polyester or polyesteramide has an acid moiety of from about 75 to about 84 mole % isophthalic acid and conversely from about 25 to about 16 mole % 5-sodiosulfoisophthalic acid, and a glycol moiety of from abut 45 to about 60 mole % diethylene glycol and conversely from about 55 to about 40 mole % 1,4-cyclohexanedimethanol or ethylene glycol or mixtures thereof.

7. A water-based hair spray composition according to claim 6 wherein the polyester or polyesteramide comprises an acid moiety comprising from about 80 to about 83 mole % isophthalic acid and conversely from about 20 to about 17 mole % 5-sodiosulfoisophthalic acid, and said glycol moiety comprises from about 52 to about 56 mole % diethylene glycol and conversely from about 48 to about 44 mole % 1,4-cyclohexanedimethanol.

8. A water-based hair spray composition according to claim 5 wherein the polyester or polyesteramide has an viscosity of about 0.28 to about 0.38.

9. A water-based hair spray composition according to claim 1 comprises about 2 to about 28 weight % of a polymer blend comprising
   (a) about 99 to about 1 weight % of a water soluble polymer, and
   (b) about 1 to about 99 weight % of a water-dispersible sulfonate group-containing polyester or polyesteramide;
   about 98 to about 40 weight % of water; 0 to about 30 weight % of an alcohol; and 0 to about 5 weight % of a neutralizing base.

10. A water-based hair spray composition according to claim 9 wherein the neutralizing agent is selected from metal hydroxides and aliphatic, cyclic, or aromatic amines.

11. A water-based hair spray composition according to claim 10 wherein the neutralizing agent will obtain 65 to 100% neutralization based on acid monomer in the water soluble polymer.

12. A water-based hair spray composition according to claim 1 whereby the inclusion of the water dispersible polyester or polyesteramide improves the set time and shine of the water soluble polymer to give the aqueous hair spray the drying character, drying time and feel which approaches an alcohol-based system.

13. A water-based hair spray composition according to claim 1 wherein (a) the water soluble polymer has the formula:

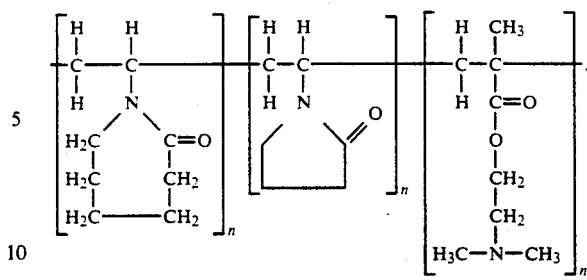
14. A water-based hair spray composition according to claim 1 wherein (b) the water dispersible polymer has the formula:
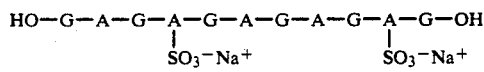
where:
A = an aromatic dicarboxylic acid moiety
G = an aliphatic or cycloaliphatic glycol residue, and
—OH = hydroxy end groups.
* * * * *

UNITED STATES PATENT OFFICE
CERTIFICATE OF CORRECTION

Patent No.  5,158,762     Dated  October 27, 1992

Inventor(s)  Deborah R. Pierce

It is certified that error appears in the above-identified patent and that said Letters Patent is hereby corrected as shown below:

Col. 3, line 4 and col. 5, line 11 (claim 1) before the first formula:

" 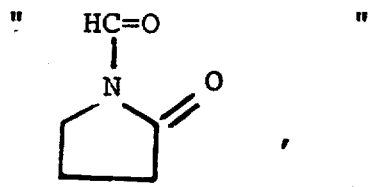 "

insert

--- 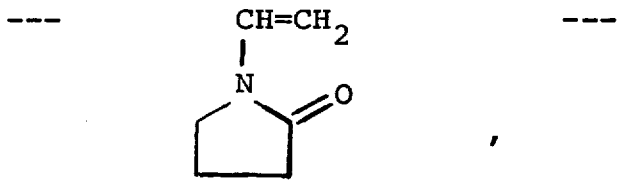 ---

Signed and Sealed this

Fourteenth Day of February, 1995

Attest:

BRUCE LEHMAN

Attesting Officer       Commissioner of Patents and Trademarks

UNITED STATES PATENT AND TRADEMARK OFFICE
CERTIFICATE OF CORRECTION

PATENT NO. : 5,158,762
DATED : October 27, 1992
INVENTOR(S) : Deborah R. Pierce

It is certified that error appears in the above-indentified patent and that said Letters Patent is hereby corrected as shown below:

In Col. 3, lines 10-15, and Col. 5, (Claim 1) lines 15-20, change the final monomer shown to include two hydrogen atoms as follows:
-- --.

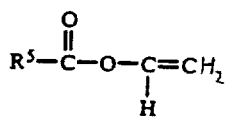

In col. 3, line 61, change "978,000" to --95,000--.

In line 65, change "1,000,000" to --100,000--.

In Col. 4, l. 40, change "B" to --G--.

In Col. 5, (Claim 1) l. 49, after "radical" change "or" to --of--.

In Col. 5, (claim 2) l. 52, after "claim" change "2" to --1--.

In Col. 6, (claim 4) l. 2, change "which" to --wherein the water soluble polymer is--.

In Col. 6, (claim 5) l. 6, change "which" to --wherein the water soluble polymer is--.

UNITED STATES PATENT AND TRADEMARK OFFICE
CERTIFICATE OF CORRECTION

PATENT NO. : 5,158,762
DATED : October 27, 1992
INVENTOR(S) : Deborah R. Pierce

It is certified that error appears in the above-indentified patent and that said Letters Patent is hereby corrected as shown below:

In Col. 6, (Claim 8) l. 32, after "claim", change "5" to --6--.

In Col. 6, (Claim 10) l. 49, after "neutralizing", change "agent" to --base--.

In Col. 6, (Claim 11) l. 54, after "neutralizing", change "agent" to --base--.

In Col. 8, (Claim 14) l. 14, after "water dispersible", delete "polymer" insert --polyester or polyesteramide--.

Signed and Sealed this

Eleventh Day of June, 1996

Attest:

BRUCE LEHMAN

Attesting Officer

Commissioner of Patents and Trademarks